(12) United States Patent
Tashiro et al.

(10) Patent No.: US 7,263,404 B2
(45) Date of Patent: *Aug. 28, 2007

(54) VISUAL RESTORATION AIDING DEVICE

(75) Inventors: Hiroyuki Tashiro, Fukuoka (JP); Yasuo Terasawa, Obu (JP)

(73) Assignee: Nidek Co., Ltd., Aichi (JP)

( * ) Notice: Subject to any disclaimer, the term of this patent is extended or adjusted under 35 U.S.C. 154(b) by 179 days.

This patent is subject to a terminal disclaimer.

(21) Appl. No.: 10/950,434

(22) Filed: Sep. 28, 2004

(65) Prior Publication Data

US 2005/0070973 A1 Mar. 31, 2005

(30) Foreign Application Priority Data

Sep. 30, 2003 (JP) .............................. 2003-340142

(51) Int. Cl.
*A61N 1/00* (2006.01)
(52) U.S. Cl. .............................. 607/54; 607/2; 607/53
(58) Field of Classification Search .................. 607/53, 607/54, 67
See application file for complete search history.

(56) References Cited

U.S. PATENT DOCUMENTS

| 4,456,012 A | * | 6/1984 | Lattin | 607/3 |
| 4,979,508 A | * | 12/1990 | Beck | 607/54 |
| 5,935,155 A | * | 8/1999 | Humayun et al. | 607/54 |

FOREIGN PATENT DOCUMENTS

| JP | A 11-511248 | 9/1999 |
| WO | WO90/00912 A1 | 2/1990 |
| WO | WO94/26209 A1 | 11/1994 |
| WO | WO96/39221 A1 | 12/1996 |
| WO | WO97/05922 A2 | 2/1997 |
| WO | WO 02/080828 A1 | 10/2002 |

* cited by examiner

*Primary Examiner*—Carl Layno
*Assistant Examiner*—Brian T. Gedeon
(74) *Attorney, Agent, or Firm*—Oliff & Berridge, PLC

(57) ABSTRACT

A visual restoration aiding device for restoring vision of a patient comprises an electrode array having a plurality of electrodes placed on or under a retina of an eye of the patient for applying an electrical stimulation pulse signal to cells constituting the retina; a photographing unit which photographs an object to be recognized by the patient; a converting unit which converts photographic data transmitted from the photographing unit to data for electrical stimulation pulse signals; and a control unit which outputs an electrical stimulation pulse signal through each electrode based on the data for electrical stimulation pulse signals so that the control unit produces pulse output through one of a first electrode and a second electrode during a halt time of pulse output through the other electrode, the first and second electrodes being arranged within a distance such that electrical stimulation pulse signals outputted therethrough at substantially the same time are likely to interfere with each other.

4 Claims, 6 Drawing Sheets

VISUAL RESTORATION AIDING DEVICE

BACKGROUND OF THE INVENTION

1. Field of the Invention

The present invention relates to a visual restoration aiding device for inducing restoration of vision.

2. Description of Related Art

In recent years, there has been research about a visual restoration aiding device using an electrode or the like placed (implanted) in an eye to induce restoration of vision by electrically stimulating cells constituting a retina. As such, there has been proposed, for example, a device designed to convert an extracorporeally photographed visual image to an optical signal or an electromagnetic signal, transmit the converted signal into the eye, and then output an electrical stimulation pulse signal (a stimulating electric current) through electrodes to stimulate the cells constituting the retina to induce visual restoration. (See U.S. Pat. No. 5,935,155). In the case of inducing the visual restoration by the electrical stimulation pulse signal provided through the electrode, it is necessary to place as many electrodes as possible at high density in order to provide more clear vision.

In a state that the electrodes are arranged at high density, however, when the electrical stimulation pulse signals are simultaneously output through adjacent electrodes, those signals are likely to interfere with each other. Such interference would become a factor that hinders the visual restoration.

SUMMARY OF THE INVENTION

The present invention has been made in view of the above circumstances and has an object to overcome the above problems and to provide a visual restoration aiding device which can properly induce restoration of vision while preventing electrical stimulation pulse signals from interfering with each other even when electrodes are arranged at high density.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visual restoration aiding device for restoring vision of a patient, the device comprising: an electrode array having a plurality of electrodes placed on or under a retina of an eye of the patient for applying an electrical stimulation pulse signal to cells constituting the retina; a photographing unit which photographs an object to be recognized by the patient; a converting unit which converts photographic data transmitted from the photographing unit to data for electrical stimulation pulse signals; and a control unit which outputs an electrical stimulation pulse signal through each electrode based on the data for electrical stimulation pulse signals so that the control unit produces pulse output through one of a first electrode and a second electrode during a halt time of pulse output through the other electrode, the first and second electrodes being arranged within a distance such that electrical stimulation pulse signals outputted therethrough at substantially the same time are likely to interfere with each other.

According to another aspect, the present invention provides a visual restoration aiding device for restoring vision of a patient, the device comprising: a plurality of electrodes placed on or under a retina of an eye of the patient; and a control unit which outputs an electrical stimulation pulse signal through each electrode so that the control unit produces pulse output through one of a first electrode and a second electrode during a halt time of pulse output through the other electrode, the first and second electrodes being arranged within a distance such that electrical stimulation pulse signals outputted therethrough at substantially the same time are likely to interfere with each other.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
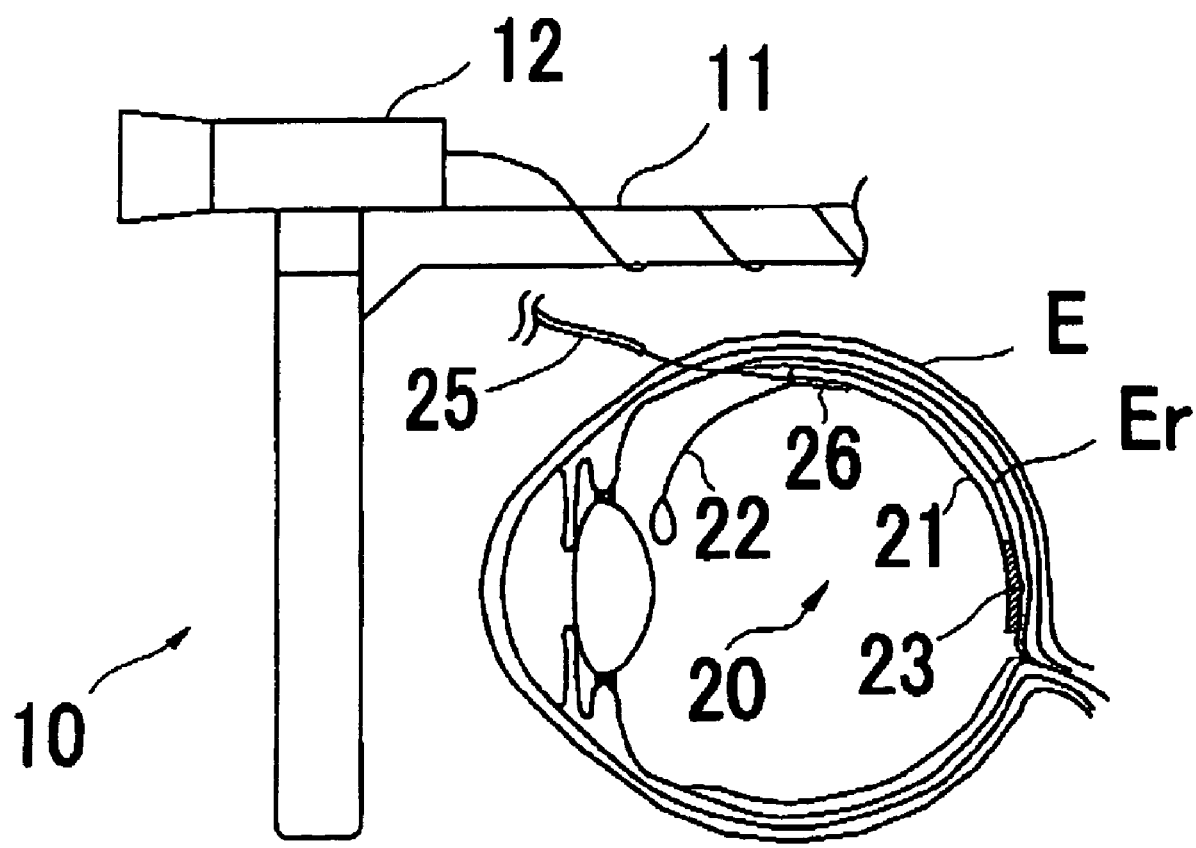
FIG. 1 is a schematic structural view of a visual restoration aiding device in a preferred embodiment according to the present invention.
Figure 2:
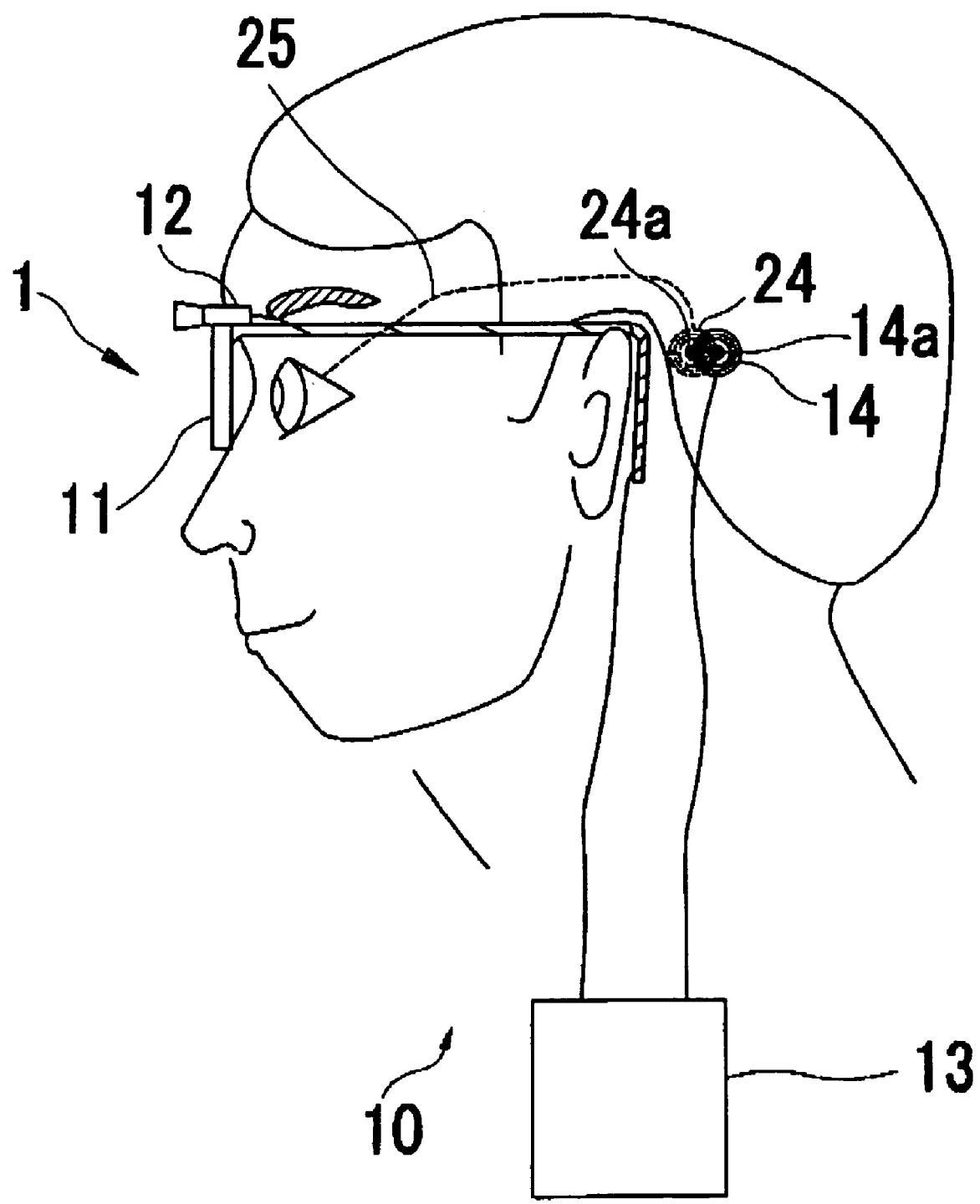
FIG. 2 is a schematic structural view of the visual restoration aiding device.
Figure 3:
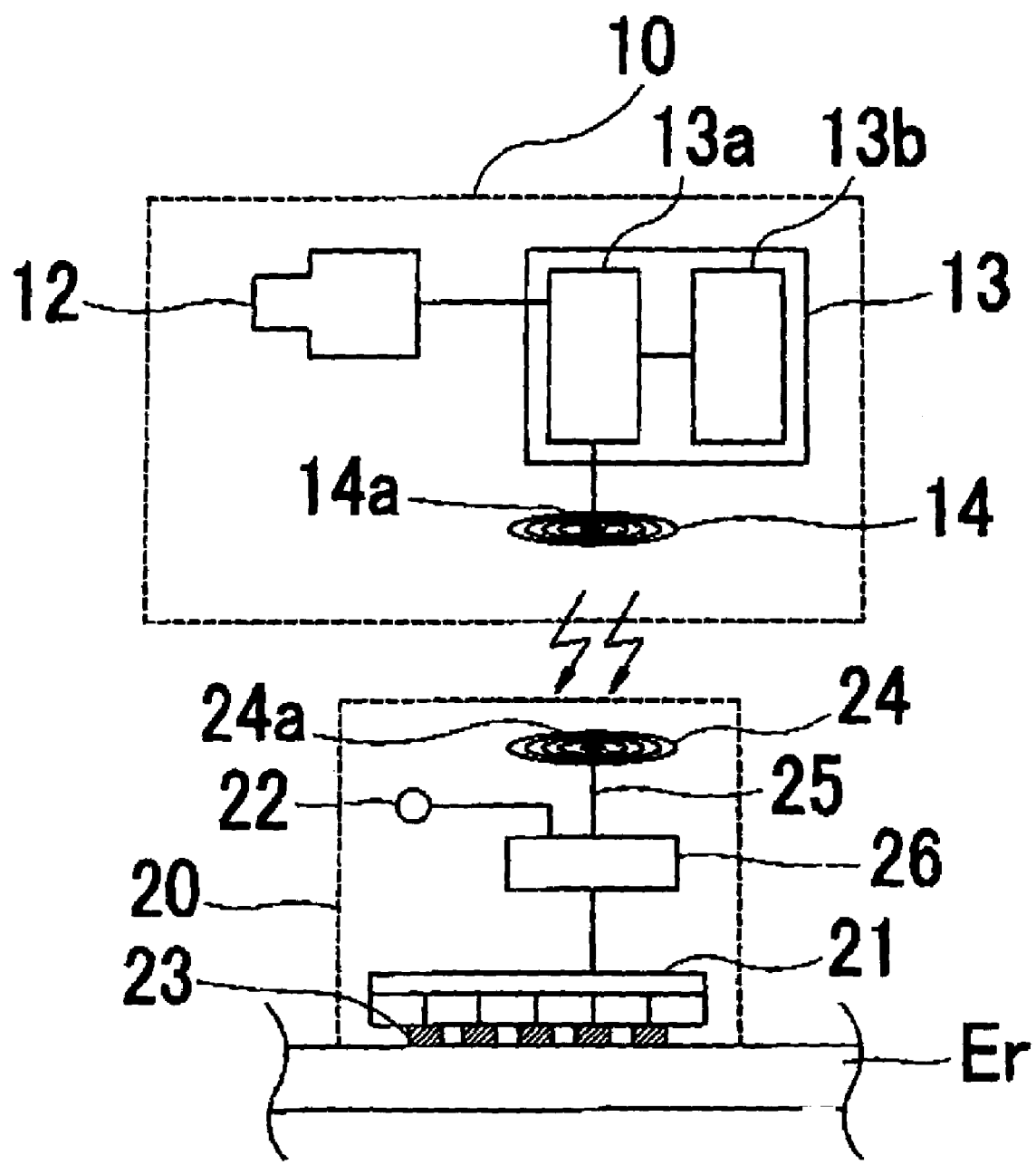
FIG. 3 is schematic block diagram of a control system in the visual restoration aiding device.

A detailed description of a preferred embodiment of a visual restoration aiding device embodying the present invention will now be given referring to the accompanying drawings. FIGS. 1 and 2 are schematic structural views of the visual restoration aiding device in the present embodiment. FIG. 3 is a schematic block diagram of a control system in the device.

The visual restoration aiding device 1 includes an external (extracorporeal) device 10 which photographs the outside world, or captures surrounding images, and an internal (intracorporeal) device 20 which applies electrical stimulation to cells constituting a retina to induce restoration of vision. The external device 10 includes a visor 11 which a patient wears, a photographing unit 12 such as a CCD camera which is mounted on the visor 11, an external unit 13, and a transmitting unit 14 including a coil, as shown in FIGS. 1 and 2. The visor 11 is shaped like eyeglasses, which the patient wears in the front of his eye E. The photographing unit 12 is mounted in the front of the visor 11 and photographs an object to be recognized by the patient.

The external unit 18 includes a pulse signal converting unit 13a for converting photographic data (video data) transmitted from the photographing unit 12 to data (information) for electrical stimulation pulse signals and a battery 13b for supplying electric power to the visual restoration aiding device 1 (that is, the external device 10 and the internal device 20). The transmitting unit 14 is used for transmitting the converted data for electrical stimulation pulse signals by the converting unit 13a and the electric power for driving the internal device 20, in the form of electromagnetic waves, to the internal device 20 by wireless communication. The transmitting unit 14 is provided at its center with a magnet 14a. This magnet 14a is used for enhancing the transmitting efficiency of the transmitting unit 14 and also to fit the position of the transmitting unit 14 to a receiving unit 24 mentioned later.

The internal device 20 includes a substrate 21 on which electrodes 23 are placed for applying the electrical stimulation pulse signals to the cells constituting the retina Er of the eye E, an indifferent electrode 22, the receiving unit 24 including a coil for receiving the electromagnetic waves from the external device 10, a cable 25, and an internal unit 26. The receiving unit 24 is provided at its center with a magnet 24a which is used for the same purpose as the magnet 14a of the transmitting unit 14.

Figure 4A:
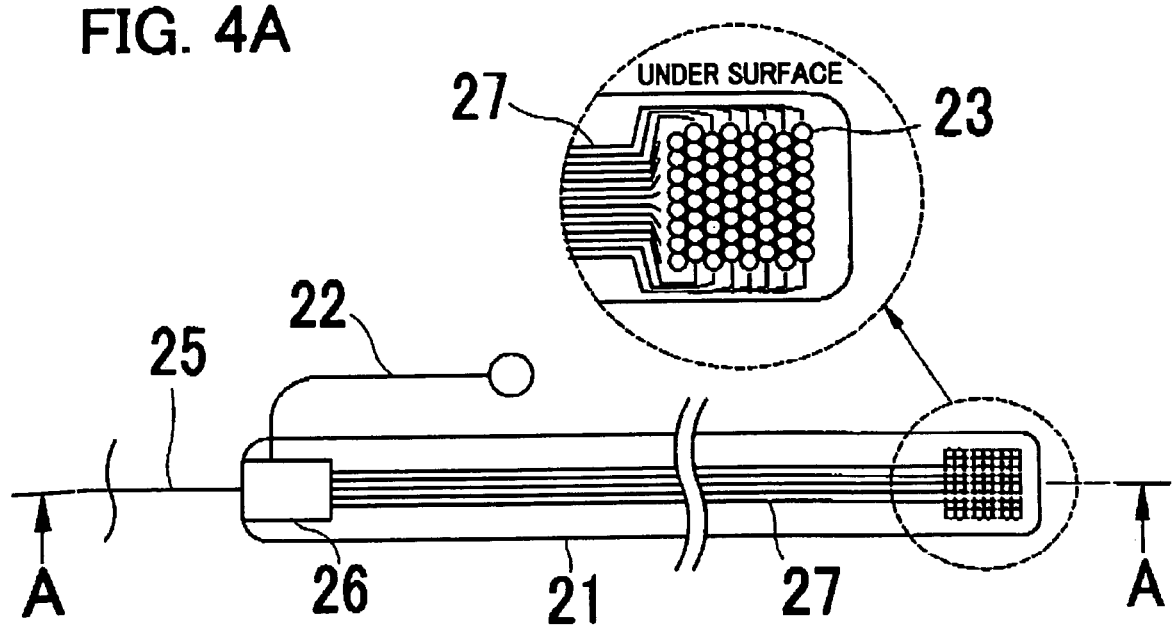
FIG. 4A is a plan view of an internal device.
Figure 4B:
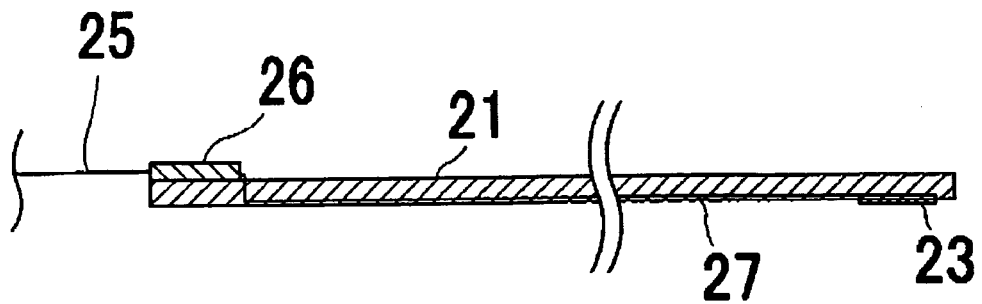
FIG. 4B is a cross-sectional view of the internal device taken along line A-A in FIG. 4A.

FIG. 4A is a plan view showing a schematic structure of the internal device 20 and FIG. 4B is a cross-sectional view of the internal device 20 taken along line A-A in FIG. 4A.

The substrate 21 is made of a flexible material having good biocompatibility, which is polyimide in the present embodiment. The substrate 21 is of a substantially long plate shape whose end (right end in FIG. 4A) is provided, on the under surface of the substrate 21 (i.e., on the back of the drawing sheet of FIG. 4A), with a multipoint electrode array having a plurality of electrodes 23 arranged at predetermined intervals (at regular intervals) for applying the electrical stimulation pulse signals to the cells constituting the retina. The electrodes 23 are arranged in a honeycomb pattern in order to minimize the intervals between the electrodes 23 as shown in FIG. 4A, particularly, in a partially enlarged figure. This arrangement contributes to increase electrode placement density, thereby achieving high spatial resolution. In the present embodiment, a total of sixty-four electrodes 23 in an 8×8 arrangement are placed on the substrate 21.

Each electrode 23 is independently connected with a corresponding electric wire (a lead wire) 27. As shown in FIG. 4B, each electric wire 27 connects between the associated electrode 23 and the internal unit 26 provided on the upper surface of the substrate 21 (i.e., on the front of the drawing sheet of FIG. 4A) at a base end (a left end in FIG. 4A) thereof. The internal unit 26 is also connected to the receiving unit 24 through the cable 25. This internal unit 26 includes a converting circuit for converting the data for electrical stimulation pulse signals transmitted via the receiving unit 24 to the electrical stimulation pulse signals and a control part which controls output of the electrical stimulation pulse signals through the electrodes 23.

To place (implant) the internal device 20 (the substrate 21) constructed as above in the eye E, it is fixedly attached to the retina Er of the eye E by a rivet-shaped tack not shown, adhesive having good biocompatibility, etc.

The following explanation is made on output control of the electrical stimulation pulse signals for visual restoration in the visual restoration aiding device constructed as above.

The external device 10 and the internal device 20 of the visual restoration aiding device 1 are attached to the eye E as shown in FIGS. 1 and 2.

The photographic data on an object photographed by the photographing unit 12 is converted by the signal converting unit 13a to the data for electrical stimulation pulse signals within a predetermined frequency band. The converted data is then transmitted in the form of electromagnetic waves by the transmitting unit 14 to the internal device 20. The data for electrical stimulation pulse signals includes the information about the electrodes 23 needed to output the electrical stimulation pulse signals and the stimulation conditions such as a frequency of the electrical stimulation pulse signals to be outputted through the electrodes 23, an amplitude (namely, intensity of, stimulation electric currents) and a stimulating time length. Simultaneously, the signal converting unit 13a converts the electric power supplied from the battery 13b to an electric power signal of a frequency band different from the frequency band of the data for electrical stimulation pulse signals and transmits it in the form of electromagnetic waves to the internal device 20.

In the internal device 20, the receiving unit 24 receives the data for electrical stimulation pulse signals and the data for electric power transmitted from the external device 10 and then transmits them to the internal unit 26. This internal unit 26 extracts a signal of the frequency band being used for the data for electrical stimulation pulse signals from among the received signals. A signal of another frequency band is supplied as the electric power for driving the internal device 20. The internal unit 26 forms electrical stimulation pulse signals to be outputted through the electrodes 23 based on the extracted data for electrical stimulation pulse signals and outputs those signals through the electrodes 23, thereby inducing the restoration of vision.

At this time, when the internal unit 26 has to output the electrical stimulation pulse signals at the same time (timing) through the electrodes 23 placed within a distance such that the electrical stimulation pulse signals outputted therethrough are likely to interfere with each other, the internal unit 26 controls the output of the electrical stimulation pulse signals so that their output timings are shifted or delayed without coinciding with one another.

Figure 5A:
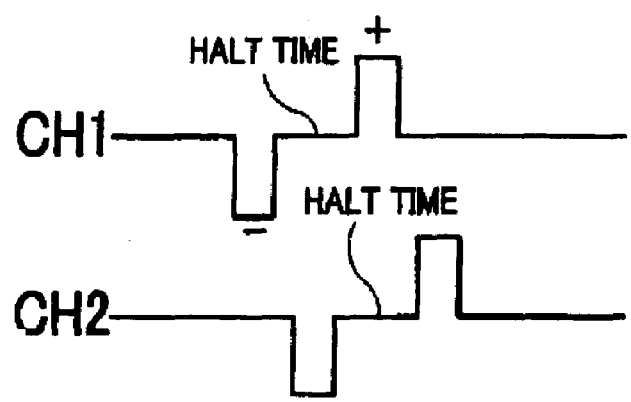
FIGS. 5A and 5B show examples of output states of two-phase electrical stimulation pulse signals through electrodes.
Figure 5B:
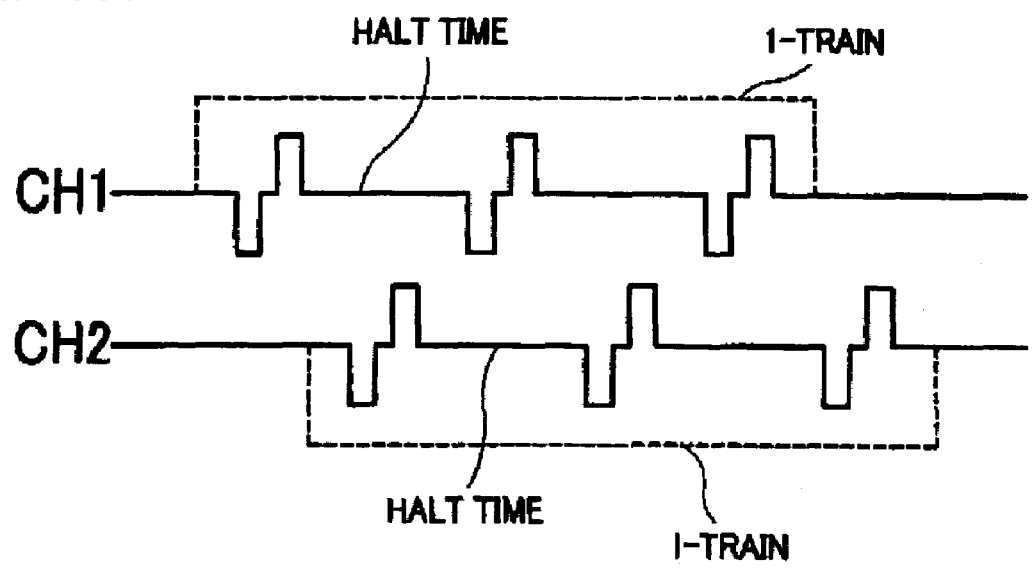

FIGS. 5A and 5B show examples of output states of two-phase electrical stimulation pulse signals through electrodes 23, for example, bipolar electrical stimulation pulse signals each having a waveform including both a negative electric current value and a positive electric current value.

The internal device 26 controls the signal output through a first electrode 23 (hereinafter, "CH1") so as to output a two-phase (bipolar) pulse waveform signal, that is, output (suck) a negative pulse and, after a halt time, output (deliver) a positive pulse. The internal device 26 also controls the signal output through a second electrode 23 (hereinafter, "CH2") so as to output a similar two-phase (bipolar) pulse waveform signal in time with the halt time (interval) of pulse output through CH1 (the two-phase (bipolar) pulse waveform signal may have a reverse waveform in positive and negative values to above). FIGS. 5A and 5B show the control of signal output through two electrodes (CH1 and CH2); in addition, similar control may be made through three or more electrodes (CH3, CH4, . . . ).

For example, as shown in FIG. 5A, a negative pulse is outputted through CH2 during the halt time of pulse output through CH1 between the negative pulse and the positive pulse. Further, a positive pulse is outputted through CH1 during the halt time of pulse output through CH2 between the negative pulse and the positive pulse.

Even where the electrical stimulation pulse signals are outputted at substantially the same time (timing) through the electrodes 23 placed within a distance such that the output pulse signals are likely to interfere with each other, the above output control makes it possible to prevent the pulse signals from interfering with each other. Accordingly, a delay of an updating rate for forming one image can be prevented even when the number of electrodes (the number of channels) is increased, thereby improving visual restoration.

Even where the electric stimulation pulse signals to be outputted through the electrode 23 for one stimulation are outputted in the form of a plurality of two-phase (bipolar) pulse waveform signals as a train stimulation, as shown in FIG. 5B, the internal unit 26 has only to output similar two-phase pulse waveform signals through CH2 in time with each halt time between the two-phase pulse waveform signals within one train outputted through CH1.

In the above embodiment, the two-phase (bipolar) electric stimulation pulse signal is outputted through each electrode 23. The present invention can also be applied to the case where a single-phase electric stimulation pulse signal is outputted through each electrode 23.

Figure 6A:
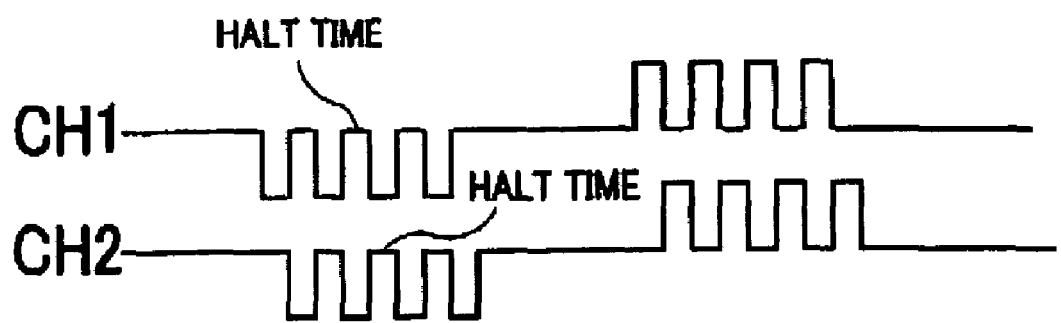
FIG. 6A shows an example of output states of single-phase electrical stimulation pulse signals through the electrodes.

FIG. 6A shows an example of output states of the single-phase electrical stimulation pulse signals through the electrodes 23. As shown in FIG. 6A, the internal unit 26 has only to output similar single-phase pulse waveform signals through CH2 in time with each halt time between the single-phase pulse waveform signals outputted through CH1.

In the embodiment using the two-phase pulse waveform signal, the strength (an absolute value of electric current) of the negative pulse and the strength of the positive pulse are substantially equal, but not limited thereto. The present invention can be applied to the case where the internal unit 26 outputs, through each electrode 23, a two-phase pulse waveform signal including a combination of a pulse that is high in strength (amplitude) and short in pulse width (namely, a High-Short (H-S) pulse) and a pulse that is low in strength (amplitude) and long in pulse width (namely, a Low-Long (L-L) pulse). This is shown in FIG. 6B.

Figure 6B:
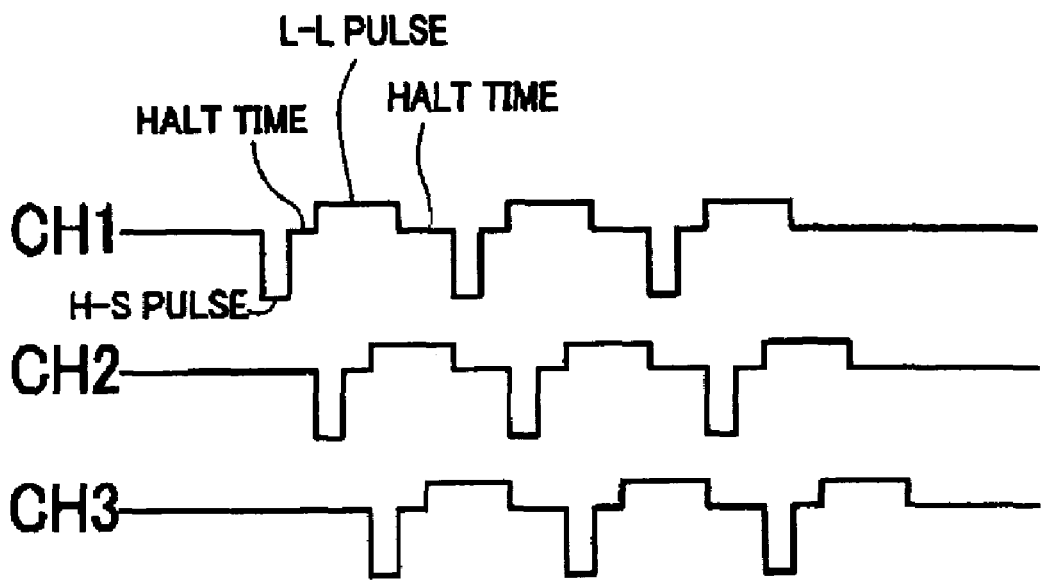
FIG. 6B shows an example of output states of two-phase electrical stimulation pulse signals through the electrodes.

As shown in FIG. 6B, in the case of outputting the two-phase pulse waveform signals including a combination of an H-S pulse and an L-L pulse through each electrode 23 (CH1, CH2, and CH3), the internal device 26 outputs those signals so that the H-S pulses do not coincide with each other. Specifically, an H-S pulse is outputted through one electrode 23 while an L-L pulse is outputted through another electrode 23. If the H-S pulses are outputted at the same time, they are likely to interfere with each other due to their high strength. Even if the H-S pulse and the L-L pulse are outputted at the same time, on the other hand, they are unlikely to interfere with each other. Even if the L-L pulses are outputted at the same time, furthermore, they are unlikely to interfere with each other because of their low strength.

It is to be noted that the manners of output control shown in FIGS. 5A and 5B and FIGS. 6A and 6B may be used in combination.

As described above, in order to output the electric stimulation pulse signals at the same time (timing) through the electrodes placed within a distance such that the outputted electric stimulation pulse signals are likely to interfere with one another, it is controlled to output the pulse waveform signals through each electrode in time with each halt time between the pulse waveform signals through another electrode. Accordingly it is possible to output the electric stimulation pulse signals through the electrodes at substantially the same time (timing) without delaying the updating rate of an image.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A visual restoration aiding device for restoring vision of a patient, the device comprising:
   an electrode array which is placeable in an eye of the patient and in which a plurality of electrodes are arranged for applying an electrical stimulation pulse signal to cells constituting the retina;
   a photographing unit which photographs an object to be recognized by the patient;
   a converting unit which converts photographic data transmitted from the photographing unit to data for electrical stimulation pulse signals; and
   a control unit which outputs a bipolar electrical stimulation pulse signal including a negative pulse and a positive pulse through each electrode based on the data for electrical stimulation pulse signals the control unit outputting the electrical stimulation pulse signals through a first electrode and a second electrode at substantially the same time by producing pulse output at shifted output timings so as to output at least one of the negative pulse and the positive pulse of the electrical stimulation pulse signal outputted through one of the first and second electrodes on the electrode array during a halt time between the negative pulse and the positive pulse of the electrical stimulation pulse signal outputted through the other electrode, the first and second electrodes being arranged within a distance such that the electrical stimulation pulse signals outputted therethrough at the same time are likely to interfere with each other.

2. The visual restoration aiding device according to claim 1, wherein one stimulation by the electrical stimulation pulse signal includes a train stimulation by a plurality of the bipolar electrical stimulation pulse signals.

3. The visual restoration aiding device according to claim 1, wherein the electrical stimulation pulse signal includes the bipolar electrical stimulation pulse signal including the negative pulse and the positive pulse different in strength, and
   the control unit produces the pulse output so that a high strength pulse through one of the first and second electrodes does not coincide with a high strength pulse through the other electrode.

4. A visual restoration aiding device for restoring vision of a patient, the device comprising:
   an electrode array which is placeable in an eye of the patient and in which a plurality of electrodes are arranged for applying an electrical stimulation pulse signal to cells constituting the retina;
   a photographing unit which photographs an object to be recognized by the patient;
   a converting unit which converts photographic data transmitted from the photographing unit to data for electrical stimulation pulse signals; and
   a control unit which outputs a bipolar electrical stimulation pulse signal including a negative pulse and a positive pulse through each electrode based on the data for electrical stimulation pulse signals, the negative pulse and the positive pulse being different in strength, the control unit outputting the electrical stimulation pulse signals through a first electrode and a second electrode at substantially the same time by producing pulse output at shifted output timings so as to output a pulse of larger strength of the electrical stimulation pulse signal outputted through one of the first and second electrodes on the electrode array at the time of output of a pulse of smaller strength of the electrical stimulation pulse signal outputted through the other electrode, the first and second electrodes being arranged within a distance such that the electrical stimulation pulse signals outputted therethrough at the same time are likely to interfere with each other.

* * * * *